United States Patent [19]

Gibbs

[11] 4,212,870

[45] Jul. 15, 1980

[54] 1-(2,6-DICHLOROBENZOYL)-3-(5-CHLORO-2-PYRIDINYL-N-OXIDE)UREA AND USE AS INSECTICIDE

[75] Inventor: Charles G. Gibbs, Shawnee Mission, Kans.

[73] Assignee: Gulf Oil Corporation, Pittsburgh, Pa.

[21] Appl. No.: 49,381

[22] Filed: Jun. 18, 1979

[51] Int. Cl.$^2$ .................. A61K 31/44; C07D 213/75
[52] U.S. Cl. .................................. 424/263; 546/304; 546/312
[58] Field of Search ................... 546/312; 424/263

[56] References Cited

FOREIGN PATENT DOCUMENTS 868228 12/1976 Belgium .................................... 424/263
2123236 12/1971 Fed. Rep. of Germany .......... 546/312

OTHER PUBLICATIONS

De Milo et al., J. Agric. Food Chem., vol. 26, pp. 164-166 (1978).
Deady, Synthetic Communications, vol. 7, p. 509 (1977).

Primary Examiner—John D. Randolph
Attorney, Agent, or Firm—Carl A. Cline

[57] ABSTRACT

A new insecticide with systemic activity when applied at the roots of plants is 1-(2,6-dichlorobenzoyl)-3-(5-chloro-2-pyridinyl-N-oxide)urea.

5 Claims, No Drawings

1-(2,6-DICHLOROBENZOYL)-3-(5-CHLORO-2-PYRIDINYL-N-OXIDE)UREA AND USE AS INSECTICIDE

DESCRIPTION OF THE INVENTION

BACKGROUND

Diflubenzuron and related insecticides, as disclosed, for example, by De Milo et al in J. Agric. Food Chem. Vol. 26, No. 1, p. 164–6 (1978) present a problem with respect to obtaining good distribution on plants and assuring effective contact with insects. For the most part, these insecticides do not have systemic activity. They are deposited on the surface of plant foliage and must be eaten by chewing insects in order to be effective. If the particle size of the deposited material is too large, insects may be able to avoid ingesting fatal amounts until they have done considerable damage.

Belgian Pat. No. 868,228 discloses a class of dihalobenzoylurea insecticides which, when applied on older foliage of a plant, for example a soya plant, will be transferred within the soya plant up to newer shoots of the plant. However, there is no transfer of the insecticide through the plant when the compound is applied to roots of soya or other plants.

STATEMENT OF THE INVENTION

I have discovered that a new compound, 1-(2,6-dichlorobenzoyl)-3-(5-chloro-2-pyridinyl-N-oxide)urea is a systemic insecticide when applied at the roots of plants, as well as being effective against chewing insects when applied to foliage. This compound has the structural formula:

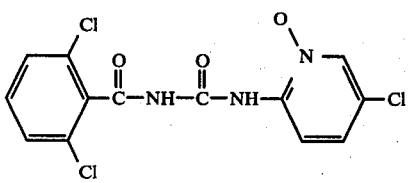

Method of Synthesis of the Insecticide

The novel compound may be prepared by reacting dichlorobenzoyl isocyanate with 2-amino-5-chloropyridine N-oxide.

The 2-amino pyridine-N-oxide is prepared as taught by L. W. Deady, Synthetic Communications, 7, 509(1977). Preparation of 1-(2,6-dichlorobenzoyl)-3-(5-chloro-2-pyridinyl-N-oxide)urea is specifically illustrated in the following example:

EXAMPLE 1

To a suspension of 3.4 g (0.024 mole) of 2-amino-5-chloropyridine-N-oxide in 50 ml of dry ethyl acetate was added all at once a solution of 5.4 g (0.025 mole) of freshly prepared 2,6-dichlorobenzoyl isocyanate in dry ethyl acetate. The mixture was allowed to stir at 25° for six hours. Filtration gave 6.2 g of product, m.p. 218°–219°. The infrared and nuclear magnetic resonance spectra were consistent with the proposed structure.

A more efficient, novel method of synthesis of the insecticide comprises the steps (a) reacting 2-amino-5-chloropyridine with an equimolar amount of 2,6-dichlorobenzoyl isocyanate in a non-reactive organic solvent to obtain 1-(2,6-dichlorobenzoyl)-3-(5-chloro-2-pyridinyl)urea and (b) reacting this material with hydrogen peroxide in acetic acid to obtain the corresponding N-oxide, as illustrated specifically in Example 2 below.

EXAMPLE 2

To a suspension of 16.7 g (0.13 mole) of 2-amino-5-chloropyridine in 250 ml of ethyl acetate was added all at once a solution of 30.0 g (0.14 mole) of 2,6-dichlorobenzoyl isocyanate in ethyl acetate. The mixture was allowed at 25° for six hours. Filtration gave 36.3 g (85%) of 1-(2,6-dichlorobenzoyl)-3-(5-chloro-2-pyridinyl)urea, m.p. 220–222°.

To a suspension of 36.3 g (0.11 mole) of 1-(2,6-dichlorobenzoyl)-3-(5-chloro-2-pyridinyl)urea in 110 ml of glacial acetic acid was added 13.8 ml (0.16 mole) of 30% hydrogen peroxide. The mixture was heated at 70° for 24 hours and then another 13.8 ml of 30% hydrogen peroxide was added. Heating was continued for another 24 hours. The mixture was cooled, 200 ml of water added, and the crude product was filtered and pressed dry. Purification was achieved by dissolving the crude product in warm dimethyl sulfoxide, filtering if necessary, and precipitating with water. Filtration and drying gave 34.9 g (88%) of the desired pyridinyl N-oxide, m.p. 218°–219°.

Use of the Insecticide

For foliar application it is desirable to apply the insecticide to infested plants so that it will be distributed as uniformly as possible. The insecticide is particularly effective against southern armyworm (*Spodoptera eridania*), a pest which moves and feeds slowly on the plants, ingesting toxic quantities of the compound. Control will therefore be most effective if the chemical is present in all areas of the plant, so as to make it available for ingestion. This is best accomplished by means of an aqueous spray of sufficient volume to wet the entire plant, the active agent being contained therein at a relatively low concentration, preferably between 30 and 500 parts per million. A 500 ppm spray mixture may be made by dissolving 25 mg of insecticide in 5 ml of acetone and adding sufficient warm 2 to 3 percent aqueous solution of octylphenoxypolyethoxyethanol emulsifier to make a total volume of 50 ml. Upon shaking, this mixture forms a uniform dispersion, suitable for spraying. Use of the insecticide is illustrated by the following specific example.

EXAMPLE 3

Bean plants were grown in vermiculite in small paper drinking cups and were sprayed to thorough wetness, each with an aqueous dispersion of the insecticide at a specific concentration. Leaves were removed from the bean plants after spraying and drying and were placed in disposable petri dishes, wherein were also placed 5 southern armyworm larvae (SA) or 5 Mexican bean beetle larvae (MBB). Observations were made on some of the petri dishes each day, as the larvae continued to feed and die. The results were rated according to the following schedule:

0—no larvae dead
1—1 to 25% dead
2—26–50% dead
3—51–75% dead
4—76–99% dead
5—100% dead Observations were recorded after expiration of two days and again after four days.

|     |       | Concentrations PPM |     |     |    |    |    |
|-----|-------|--------------------|-----|-----|----|----|----|
|     |       | 500                | 250 | 125 | 62 | 31 | 15 |
| MBB | 48 hr | 0                  |     |     |    |    |    |
|     | 96 hr | 0                  | 0   | 0   | 0  | 0  | 0  |
| SA  | 48 hr | 5                  |     |     |    |    |    |
|     | 96 hr | 5                  | 5   | 5   | 5  | 2  | 2  |

EXAMPLE 4

The primary leaves of Henderson bush lima bean plants were dipped into a 1000 ppm solution of insecticide. The plants were watered for one week to give the new foliage time to grow. The new foliage (first trifoliate) was then clipped, a moist cotton ball placed on the petiole, and placed in a petri dish. Five southern armyworm second instar larva were placed in each dish. Fresh (treated) food and water were placed in each dish as needed. Treatments consisted of insecticide in three surfactants: Triton TX-100, Tergitol TMN-10, & Regulaid. All chemicals were dissolved in 5 ml of acetone to aid in forming a suspension. Each surfactant solution was also placed in petri dishes on leaves as a check. In the first test the plants were allowed to absorb the solution for 24 hours. In the second test they were allowed 3 days. The part of the leaf where the cotton was placed was removed with a cork borer. Five southern armyworms, second instar larva were added to each dish. Number of dead larvae/dish were counted after 24, 48 and 96 hours.

The second experiment was identical except plants were held 1 week after treatment and ratings were made after 48, 96 and 144 hours. Results are tabulated below.

| Experiment No. 1 Rating (All Treatments 1000 ppm)[1] | | | |
|---|---|---|---|
| Treatment | 24 hours | 48 hours | 96 hours |
| Diflubenzuron | | | |
| (Acetone + TX-100)[2] | 0 | 0 | 0 |
| 1-(2,6-Dichlorobenzoyl)-3-(5-chloro-2-pyridinyl-N-oxide)urea | | | |
| (Acetone + TMN-10)[3] | 0 | 1 | 3 |
| (Acetone + Regulaid)[4] | 0 | 2 | 2 |
| (DMSO + TX-100)[5] | 0 | 0 | 1 |
| Check (No insecticide) | 0 | 0 | 0 |

| Experiment No. 2 | | | |
|---|---|---|---|
|  | 48 hours | 96 hours | 144 hours |
| 1-(2,6-Dichlorobenzoyl)-3-(5-chloro-2-pyridinyl-N-oxide)urea | | | |
| (Acetone + TMN-10) | 0 | 4 | 5 |
| (Acetone + Regulaid) | 0 | 0 | 1 |
| Diflubenzuron | | | |
| (Acetone + TX-100) | 0 | 1 | 1 |
| Untreated Check | 0 | 0 | 1 |

[1]All solutions contain 500 ppm of surfactant.
[2]TX-100 is Triton X-100, an octylphenoxy polyethoxyethanol wetting agent.
[3]TMN-10 is Tergitol TMN-10, a trimethylnonyl polyethylene glycol ether, an emulsifier, wetting and dispersing agent.
[4]Regulaid is a proprietary non-ionic wetting agent of Kalo Laboratories, Inc.
[5]DMSO is dimethylsulfoxide.

The best indication of translocation within the leaf was obtained with the insecticide of this invention, assisted by a non-ionic wetting agent (TMN-10) which is a product of condensation of trimethylnonanol with 10 moles of ethylene oxide. Diflubenzuron showed substantially no ability to translocate within the leaf.

EXAMPLE 5

Systemic activity was demonstrated as follows:
Henderson bush lima beans were grown in 5 oz dixie cups. Beans tested at first primary leaf stage by (1) adding 50 ml of the candidate compound formulated with Triton X-100 water at concentrations of 4 to 62 ppm, (2) allowing four days for transfer of the chemical from the root system to the leaves, (3) clipping the leaves and placing in petri dishes, (4) adding second instar, SA, larvae to each dish, and (5) observing for mortality in 96 hours.

Results are tabulated below.

| Systemic Activity | |
|---|---|
| CONC ppm | SA mortality |
| 62 | 5 |
| 31 | 5 |
| 15 | 5 |
| 8 | 5 |
| 4 | 3 |

It is understood that an insecticidally effective amount of chemical is an amount sufficient to kill enough insect pests so as to achieve a beneficial effect and is usually substantially less than the preferred or most effective rate of application, in which the cost of the method is balanced against the increase in value of the crop for maximum overall economic benefit. There may be specific situations in which it is desirable to use considerably more than an effective or a preferred amount of pesticide. An example of such a situation is an integrated pest control program in which many farmers in a very large area are engaged in an effort to substantially eliminate a pest from the entire region. Ordinarily, however, the use of excessive amounts is not economically beneficial. In the case of insects, the near-elimination of a particular species from the area may result in the creation of an insecticide resistant strain of the pest. It is better, in general, to not try for total kills unless there is a good chance of success of a program to totally eliminate the pest.

I claim:
1. The method of killing insect pests on plants which comprises applying to the infested plants an insecticidally effective amount of 1-(2,6-dichlorobenzoyl)-3-(5-chloro-2-pyridinyl-N-oxide)urea.
2. The method according to claim 1 in which the insect pests are southern armyworm larvae.
3. The method according to claim 1 in which an insecticidally effective amount of 1-(2,6-dichlorobenzoyl)-3-(5-chloro-2-pyridinyl-N-oxide)urea is applied to the roots of the plants.
4. The method of manufacturing 1-(2,6-dichlorobenzoyl)-3-(5-chloro-2-pyridinyl-N-oxide)urea comprising the steps
   (a) reacting 2-amino-5-chloropyridine with an equimolar amount of 2,6-dichlorobenzoyl isocyanate in a non-reactive organic solvent to obtain 1-(2,6-dichlorobenzoyl)-3-(5-chloro-2-pyridinyl)urea and,
   (b) reacting said product of step (a) with hydrogen peroxide in acetic acid to obtain the corresponding N-oxide compound.
5. 1-(2,6-Dichlorobenzoyl)-3-(5-chloro-2-pyridinyl-N-oxide)urea.

* * * * *